United States Patent [19]
Gregson et al.

[11] 3,991,046
[45] Nov. 9, 1976

[54] PENICILLIN ANTIBIOTICS

[75] Inventors: Michael Gregson, London; Martin Christopher Cook; Gordon Ian Gregory, both of Chalfont St. Peter, all of England

[73] Assignee: Glaxo Laboratories Limited, Greenford, England

[22] Filed: Sept. 11, 1975

[21] Appl. No.: 612,262

Related U.S. Application Data

[60] Division of Ser. No. 466,780, May 3, 1974, Pat. No. 3,926,957, which is a division of Ser. No. 274,602, July 24, 1972, abandoned, which is a continuation-in-part of Ser. No. 221,057, Jan. 26, 1972, abandoned.

[30] Foreign Application Priority Data

July 7, 1972 United Kingdom............... 32004/72

[52] U.S. Cl. ............................................. 260/239.1
[51] Int. Cl.² ...................................... C07D 499/68
[58] Field of Search ............................. 260/239.1

[56] References Cited
FOREIGN PATENTS OR APPLICATIONS
1,159,449   1963   Germany ....................... 260/239.1

OTHER PUBLICATIONS
Chem. Abstr., vol. 70, Col. 77850(c) (1969).
Arkiv Forkemi, 22(33), pp. 451–467 (1964).
Acta Chemsca Scandinavica 19, pp. 281–299 (1965).

*Primary Examiner*—Gerald A. Schwartz
*Attorney, Agent, or Firm*—Bacon & Thomas

[57] ABSTRACT

The invention provides novel antibiotic compounds which are 6β-acylamidopenam-3-carboxylic acids and non-toxic derivatives thereof, characterized in that the acylamido group has the structure

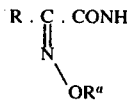

where R is a hydrogen atom or an organic group and $R^a$ is a hydrogen atom or an acyl group. The compounds are syn isomers or exist as mixtures containing at least 75% of the syn isomer. These antibiotic compounds possess high antibacterial activity against a range of gram positive and gram negative organisms coupled with particularly high stability to β-lactamases produced by various gram negative organisms. The invention is also concerned with the administration of the compounds.

2 Claims, No Drawings

PENICILLIN ANTIBIOTICS

CROSS REFERENCE TO RELATED APPLICATION

This application is a division of application Ser. No. 466,780, filed May 3, 1974, and now U.S. Pat. No. 3,926,957, which is in turn a division of application Ser. No. 274,602, filed July 24, 1972, and now abandoned, which is in turn a continuation-in-part of application Ser. No. 221,057, filed Jan. 26, 1972 and now abandoned.

This invention is concerned with improvements in or relating to antibiotics of the penicillin series.

The penicillin compounds referred to in this specification are generally named with reference to penam (*J. Amer. Chem. Soc.* 1953, 75, 3293).

As is well known, antibiotics of the penicillin series are 6β-acylamidopenam-3-carboxylic acids and their various non-toxic derivatives e.g. salts, esters, amides, hydrates or the corresponding sulphoxides. Such antibiotics may, for example, carry substituents on at least one of the gem-dimethyl groups normally present at the 2-position.

The new compounds of the present invention are characterized in that said acylamido group of the penicillin antibiotic is an α-hydroxyiminoacylamido or α-acyloxyiminoacylamido group, the compounds being syn isomers or mixtures wherein the syn isomeric form predominates.

According to one embodiment of the invention, therefore, we provide compounds selected from the group consisting of 6β-acylamidopenam-3-carboxylic acids and nontoxic derivatives thereof characterized in that said acylamido group has the structure:

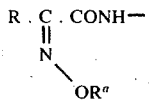

where R is a hydrogen atom or an organic group and $R^a$ is a hydrogen atom or an acyl group, said compounds being syn isomers or existing as mixtures containing at least 75% of the syn isomer.

The compounds of the invention are defined as having the syn (cis) isomeric form as regards the configuration of the group $OR^a$ with respect to the carboxamido group. Preferably, the mixtures of isomers contain at least 90% of the syn isomer and not more than 10% of the anti isomer.

In this specification, the syn configuration is structurally denoted thus:-

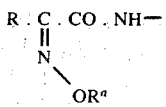

and the anti configuration thus:

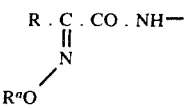

These configurations are allocated on the basis of the work of Ahmad and Spencer, *Can.J.Chem.*, 1961, 39, 1340.

The compounds of the invention may be defined by the formula:-

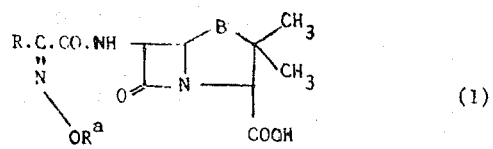

where R and $R^a$ have the above-defined meanings and B is >S or >S → 0, preferably >S. The invention also includes compounds not specifically embraced by formula (I), e.g. 2β-acetoxymethyl penicillins.

The term "non-toxic" as applied to the derivatives of the compounds of the invention means those derivatives which are physiologically acceptable in the dosage at which they are administered.

Salts which may be formed, where applicable, from the compounds according to the invention include (a) inorganic base salts such as alkali metal, e.g. sodium and potassium, alkaline earth metal e.g. calcium, and organic base, e.g. procaine, phenylethylbenzylamine and dibenzylethylene diamine, salts and (b) acid addition salts e.g., with hydrochloric, hydrobromic, sulphuric, nitric, phosphoric, toluene-p-sulphonic and methane sulphonic acids. The salts may also be in the form of resinates, formed e.g., with a polystyrene resin containing amino, quaternary amino, or sulphonic acid groups, or a resin containing carboxyl groups, e.g. a polyacrylic acid resin. The resin may if desired be cross-linked, e.g. it may be a copolymer of styrene and divinyl-benzene containing the appropriate groups. Additionally, the derivatives may be in the form of a chelate with a heavy metal such as iron or copper.

The compounds of the invention, including the non-toxic derivatives thereof, are characterized by their high antibacterial activity against a range of grampositive and gram-negative organisms coupled with particularly high stability of β-lactamases produced by various gram negative organisms.

The group $R^a$ in the above formulae, when it is acyl, may be chosen from a wide variety of possible groups. Thus the group $R^a$ may be a carboxylic acyl group $R^cCO$ having from 1 to 20 carbon atoms. In particular $R^c$ may be an aliphatic, cycloaliphatic or aromatic group or it may be such an organic group linked to the carbonyl group through an oxygen atom, a sulphur atom or an imino group. Such an aliphatic, cycloaliphatic or aromatic group may be substituted by halogen (F, Cl, Br or I), amino, nitro, $C_1$–$C_6$ alkyl, $C_1$–$C_6$ alkoxy etc.

Particular examples of $R^a$ include alkanoyl, alkenoyl and alkynoyl of up to 7 carbon atoms e.g. acetyl, propionyl, butyryl, acrylyl, crotonyl; substituted, e.g. halogenated (F, Cl, Br, I) or amino or substituted amino derivatives of such groups e.g. chloroacetyl, dichloroacetyl or β-aminopropionyl; alkoxycarbonyl of up to 7 carbon atoms e.g. ethoxycarbonyl, and t-butoxycarbonyl; substituted alkoxycarbonyl e.g. 2,2,2-trichloroethoxycarbonyl; alkylthiocarbonyl of up to 7 carbon atoms and substituted derivatives thereof; aralkyloxycarbonyl e.g. benzhydryloxycarbonyl and benzyloxycarbonyl; $C_7$–$C_{13}$ aroyl e.g. benzoyl and substituted, e.g. nitrated derivatives of such groups e.g. nitrobenzoyl; and substituted or unsubstituted carbamoyl or thiocarbamoyl i.e. compounds in which the group $R^a$ has the formula $(R^b)_2N.CO-$ or $(R^b)_2N.CS-$ and $R^b$ is the same or different and each is a hydrogen atom or a substituent such as alkyl of 1–7 carbon atoms e.g. ethyl or methyl and substituted, e.g. halogenated, alkyl of 1–7 carbon atoms e.g. chloroethyl, or $R^u$, where $R^u$ has the meaning defined below.

The group R in the above general formulae may be chosen from the following list which is not intended to be exhaustive:- i. Hydrogen, ii. $R^u$, where $R^u$ is aryl (carbocyclic or heterocyclic), cycloalkyl, substituted aryl, substituted cycloalkyl, cycloalkadienyl, or a non-aromatic or mesionic group. Examples of this group include phenyl; naphthyl; phenyl or naphthyl substituted by halo e.g. chloro or bromo, hydroxy, lower alkyl e.g. methyl, nitro, amino, lower alkylamino e.g. methylamino, diloweralkyl amino e.g. dimethylamino, lower alkanoyl e.g. acetyl, lower alkanoylamido, lower alkoxy e.g. methoxy or ethoxy. or lower alkylthio e.g. methylthio; a 5- or 6-membered heterocyclic group containing at least one hetero atom selected from S, N and O e.g. thien-2-yl,thien3-yl, furyl, pyridyl, 3- or 4-isoxazolyl; substituted 3- or 4-isoxazolyl e.g. 3-aryl-5-methylisoxazol-4-yl, the aryl group being e.g. phenyl or halophenyl; cyclohexyl; cyclopentyl; sydnone; and cyclohexadienyl.

iii. $R^u(CH_2)_mQ_n(CH_2)_p$ where $R^u$ has the above defined meaning and $m$ is 0 or an integer from 1 to 4, $n$ is 0 or 1, $p$ is an integer from 1 to 4 and Q is S. O or NR wherein R is hydrogen or an organic group e.g. alkyl such as methyl or aryl such as phenyl. Examples of this group include methyl, ethyl or butyl substituted by the various specific $R^u$ groups listed under (ii) e.g. benzyl and the appropriate substituted benzyl group.

iv. $C_nH_{2n+1}$ wherein n is an integer from 1 to 7. The group may be straight or branched and, if desired, may be interrupted by an oxygen or sulphur atom or the group NR wherein R is hydrogen or an organic group e.g. alkyl such as methyl or aryl such as phenyl; or be substituted by a cyano, carboxy, alkoxycarbonyl, hydroxy or carboxycarbonyl (HOOC.CO.) group or by a halogen atom. Examples of such groups include hexyl, heptyl, butylthiomethyl, cyanomethyl or trihalomethyl.

v. $c_nH_{2n-1}$ where $n$ is an integer from 2 to 7. The group may be straight or branched and, if desired, may be interrupted by an oxygen or sulphur atom or the group NR wherein R is hydrogen or an organic group e.g. alkyl such as methyl or aryl such as phenyl. An example of such a group is vinyl or propenyl.

vi. $C_nH_{2n-3}$ where n is an integer from 2 to 7. An example of such a group is ethynyl.

vii. Miscellaneous carbon-linked organic groups including cyano, amido and lower alkoxycarbonyl.

Preparation

The compounds according to the invention may be prepared by any convenient method. According to one embodiment of the invention we provide a process for the preparation of a compound of the formula

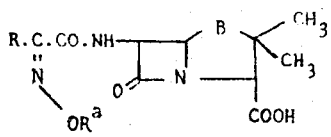

(I)

(wherein R is a hydrogen atom or an organic group, $R^a$ is hydrogen or an acyl group and B is $>S$ or $>S \rightarrow O$) and derivatives thereof, which comprises either (A) condensing a compound of the formula

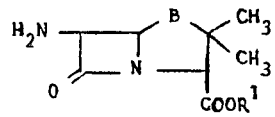

(II)

(wherein B has the above defined meaning and $R^1$ is hydrogen or a carboxyl blocking group) with an acylating agent, advantageously the syn isomer, corresponding to the acid

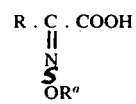

(III)

(wherein R and $R^a$ have the above defined meanings) or with an acylating agent corresponding to an acid which is a precursor for the acid (III) and converting the resulting precursor acyl group into the desired acyl group; or (B) reacting a compound of the formula

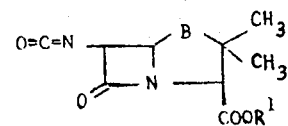

(IV)

(wherein B and $R^1$ have the above defined meaning except that $R^1$ is not hydrogen) with an acid of formula (III) wherein $R^a$ is not hydrogen; whereafter, if necessary and desired in each instance, any of the following reactions (C) are carried out (i) conversion of a precursor for the desired group into that said group

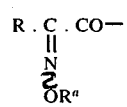

ii. removal of any carboxyl blocking groups and (iii) reduction of a compound in which Z is $>S \rightarrow O$ to form the desired $Z=>S$ compound; and (D) recovering the desired compound of formula (I), if necessary after separation of isomers.

Salts of the compounds according to the invention may be formed in any convenient way. For example base salts may be formed by reaction of the penicillin acid with sodium or potassium 2-ethylhexanoate.

In practice it is convenient to condense an acylating agent corresponding to the acid

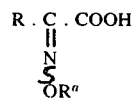

(III)

where R and $R^a$ have the above defined meanings, with an amino compound

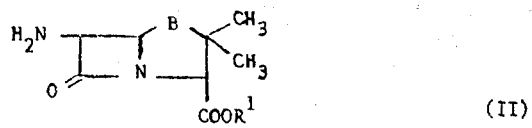

(II)

[where B has the above defined meaning and $R^1$ is hydrogen or a carboxyl blocking group e.g. the residue of an ester-forming alcohol (aliphatic or araliphatic), phenol, silanol, stannanol or acid] the condensation, if desired, being effected in the presence of a condensation agent, and being followed, if necessary, by removal of the group $R^1$. There may also be used a derivative of the amino compounds such as a salt e.g. a tosylate.

Compounds in which $R^a$ is hydrogen may be prepared indirectly and compounds in which $R^a$ is not hydrogen may be prepared directly by employing as the acylating agent an acid halide, particularly an acid chloride or bromide. In the preparation of a compound in which $R^a$ is hydrogen by this technique an additional step will be necessary in which the acyl group $R^a$ is removed to yield the hydroxyimino compound. The acylation may be effected at temperatures of from −50 to +50° C, preferably from −20 to +20° C e.g. about 0° C. The acylating agent may be prepared by reacting the acid (III) in which $R^a$ is not hydrogen with a halogenating agent e.g. phosphorus pentachloride, thionyl chloride or oxalyl chloride. The acylation may be effected in aqueous or non-aqueous media and suitable media include an aqueous ketone such as aqueous acetone, an ester e.g. ethyl acetate, or an amide e.g. dimethylacetamide, or a nitrile e.g. acetonitrile, or mixtures thereof.

Acylation with an acid halide may be effected in the presence of an acid binding agent e.g. a tertiary amine (e.g. triethylamine or dimethylaniline), an inorganic base (e.g. calcium carbonate or sodium bicarbonate) or an oxirane, which binds hydrogen halide liberated in the acylation reaction. The oxirane is preferably a lower-1, 2-alkylene oxide e.g. ethylene oxide or propylene oxide.

When using the free acid form of a compound of formula (III) and, if desired, where $R^a$=H, suitable condensing agents for use in the preparation of the compounds according to the invention include carbodiimides, for example N,N'-diethyl-, dipropyl- or diisopropylcarbodiimide, N,N'-dicyclohexylcarbodiimide, or N-ethyl-N'-γ-dimethylaminopropylcarbodiimide; a suitable carbonyl compound, for example carbonyldiimidazole; or an isoxazolinium salt, for example, N-ethyl-5-phenylisoxazolinium-3'-sulphonate and N-t-butyl-5-methylisoxazolinium perchlorate. The condensation reaction is desirably effected in an anhydrous reaction medium, e.g. methylene chloride, dimethylformamide or acetonitrile, since one may then regulate more precisely reaction parameters such as temperature.

Alternatively, acylation may be effected with other amide-forming derivatives of the free acid such as, for example, a symmetrical anhydride or mixed anhydride, e.g. with pivalic acid or formed with a haloformate, e.g. a lower alkylhaloformate. The mixed or symmetrical anhydrides may be generated in situ. For example, a mixed anhydride may be generated using N-ethoxycarbonyl-2-ethoxy-1, 2-dihydroquinoline. Mixed anhydrides may also be formed with phosphorus acids (for example phosphoric or phosphorous acids), sulphuric acid or aliphatic or aromatic sulphonic acids (for example p-toluene sulphonic acid). Another convenient acylating agent is an activated ester e.g. a compound of the formula

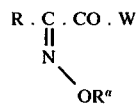

(V)

where W, is for example, azide, oxysuccinimide, oxybenztriazole, pentachlorophenoxy or p-nitrophenoxy.

One may prepare compounds according to the invention in which $R^a$ = H by condensing an acylating agent corresponding to the acid (III) in which $R^a$ is not hydrogen but is a group which can be readily removed to yield the desired group =N—OH with a compound of formula II. The $R^a$ group is removed subsequently, if desired in conjunction with the removal of the group $R^1$. Illustrative of such readily removable $R^a$ groups are acetyl, if desired having at least one electron-withdrawing group on the α-carbon atom e.g. trichloroacetyl, dichloroacetyl, monochloroacetyl, trifluoroacetyl, difluoroacetyl and monofluoroacetyl; formyl; benzhydryloxycarbonyl, benzyloxycarbonyl, t-butoxycarbonyl and 2,2,2-trichloroethoxycarbonyl. The removal of such groups may for example be effected under mildly basic conditions. Thus, for example, an acetyl group may be removed by means of treatment with aqueous alkali. Halogenated acetyl groups may be removed by means of aqueous bicarbonate and, additionally, chloracetyl can be removed using a nucleophile such as a thiourea. Benzhydryloxycarbonyl and t-butoxycarbonyl groups can be removed using trifluoroacetic acid with or without anisole, 2,2,2-Trichloroethoxycarbonyl may be removed by means of a reducing agent such as zinc/acetic acid or zinc/formic acid. It will be appreciated that although the preparation of compounds having readily removable $R^a$ groups affords a convenient route to hydroximino compounds, compounds with such $R^a$ groups are also compounds according to the invention and may possess desirable properties in their own right.

Alternatively the compound of formula (I) may be prepared from a compound of formula

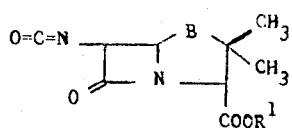

(IV)

where B and $R^1$ have the above defined meanings (except that $R^1$ is not H) by reaction with an acid of formula (III) (where $R^a$ is not H) and subsequently removing the groups $R^1$ and, if desired, $R^a$ (see for example Dutch Patent Application No. 6808622).

The reaction of the compound of formula (II) or (IV) may be carried out towards the end of the preparative sequence, the only additional reactions being deprotection reactions and purifications.

Compounds of formula I where $R^a$ = acyl may be obtained from the corresponding compounds of formula I where $R^a$ = H or from esters thereof (i.e. having at the 3-position a group COOR$^1$, R$^1$ having the above defined meaning) by acylation. Acylation may be effected in any convenient manner e.g. using an acid halide, symmetrical or mixed anhydride, ketene, acyl azide or carbodiimide (when the 3-carboxy group is protected) corresponding to the acid R$^a$OH. Alternatively the acylation may be effected by means of a haloformate for example a chloroformate such as ethylchloroformate whereupon one will obtain carbonates or by means of an isocyanate R$^b$NCO for example 2-chloroethyl isocyanate whereupon one will obtain carbamates in which OR$^a$ has the formula R$^b$NHCO.O- where R$^b$ has the above defined meaning. The acylation may be catalysed e.g. by a base such as triethylamine, diethylaniline, pyridine, propylene oxide, magnesium oxide, sodium carbonate or calcium carbonate. The acylation may be effected in an organic solvent. Suitable solvents include halogenated hydrocarbons e.g. methylene chloride; cyclic ethers e.g. dioxan or tetrahydrofuran; nitriles e.g. acetonitrile; nitrohydrocarbons e.g. nitromethane; esters e.g. ethyl acetate; or the acylating agent itself. The acylation may be effected at a temperature of −10° to +100° C, preferably 0° to 50° C advantageously 0° to 30° C. After the acylation has been effected the group R$^1$ is removed, if necessary.

If desired, one can first prepare a compound of formula

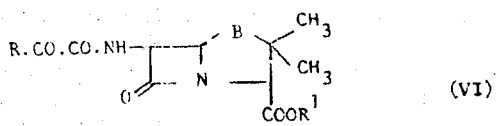

(VI)

(where R, R$^1$ and B have the above defined meanings) and then effect reaction of the compound of formula (VI) with R$^a$O.NH$_2$ (R$^a$ having the above defined meaning), followed, if necessary by removal of the group R$^1$. The reaction product may be separated into syn and anti isomers before or after removal of R$^1$.

One may prepare compounds of formula (1) wherein R is an activating group such as cyano or pyridyl by a technique involving nitrosation. Thus a compound possessing the acylamido group.

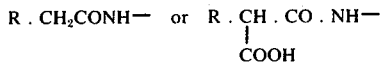

may be nitrosated using, for example, nitrous acid (which may be prepared in situ by reaction of an alkali metal nitrite with a weak acid e.g. acetic acid), nitrosyl chloride, or an organic nitrosating agent e.g. an alkyl, cycloalkyl, aryl or aralkyl nitrite. In the case of nitrosation of a compound containing the group

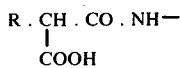

concomitant decarboxylation will occur. Separation of syn and anti-isomers may be necessary after the nitrosation reaction.

Compounds of the formula (II) may be employed as esters; those of formula (IV) are esters. One may also use the free amino acid or an acid addition salt of the free amino acid or ester thereof. Salts which may be used include acid addition salts e.g. with hydrochloric, hydrobromic, sulphuric, nitric, phosphoric, toluene-p-sulphonic and methane sulphonic acids.

The ester may be formed with an alcohol, phenol, silanol or stannanol having up to 20 carbon atoms which may readily be split off at a later stage of the overall reaction.

Any esterifying group substituting the 4-carboxyl group of a compound of formula (II), (IV) or (VI) is preferably formed with an alcohol (aliphatic or aralipatic), phenol, silanol, stannanol or acid which may readily be split off at a later stage of the reaction.

Suitable esters thus include compounds containing as ester group a group selected from the following list which is not intended to be an exhaustive list of possible ester groups.

i. - COOCR$^a$R$^b$R$^c$ wherein at least one of R$^a$, R$^b$ and R$^c$ is an electron-donor e.g. p-methoxyphenyl, 2,4,6-trimethylphenyl, 9-anthryl, methoxy, acetoxy, or fur-2-yl. The remaining R$^a$, R$^b$ and R$^c$ groups may be hydrogen or organic substituting groups. Suitable ester groups of this type include p-methoxybenzyloxycarbonyl and 2,4,6-trimethylbenzyloxy carbonyl.

ii. - COOCR$^a$R$^b$R$^c$ wherein at least one of R$^a$, R$^b$ and R$^c$ is an electron-attracting group e.g. benzoyl, p-nitrophenyl, 4 pyridyl, trichloromethyl, tribromomethyl, iodomethyl, cyanomethyl, ethoxycarbonylmethyl, arylsulphenylmethyl, 2-dimethylsulphoniumethyl, o-nitrophenyl or cyano. The remaining R$^a$, R$^b$, and R$^c$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

iii. COOCR$^a$R$^b$R$^c$ wherein at least two of R$^a$, R$^b$ and R$^c$ are hydrocarbon such as alkyl e.g. methyl or ethyl, or aryl e.g. phenyl and the remaining R$^a$, R$^b$ and R$^c$ group. if there is one, is hydrogen. Suitable esters of this type include t-butyloxycarbonyl, t-amyloxycarbonyl, diphenylmethoxycarbonyl and triphenylmethoxycarbonyl.

iv. COOR$^d$ wherein R$^d$ is adamantyl, 2-benzyloxyphenyl, 4-methylthiophenyl, tetrahydrofur-2-yl or tetrahydropyran-2-yl.

v. Silyloxycarbonyl groups obtained by reaction of a carboxyl group with a derivative of a silanol. The derivative of a silanol is conveniently a halosilane or a silazane of the formula R$^4_3$SiX, R$^4_2$SiX$_2$; R$^4_3$Si.NR$^4_2$; R$^4_3$Si.NH.SiR$^4_3$; R$^4_3$Si.NH.COR$^4$; R$^4_3$Si.NH.CO.NH.SiR$^4_3$; R$^4$NH.CO.NR$^4$.SiR$^4_3$; or R$^4$C(OSiR$^4_3$): NSiR$^4_3$ where X is a halogen and the various groups R$^4$, which can be the same or different, represent hydrogen atoms or alkyl, e.g. methyl, ethyl, n-propyl, iso-propyl; aryl, e.g. phenyl; or aralkyl e.g. benzyl groups. Preferred derivatives of silanols are silyl chlorides such as for example trimethylchlorosilane and dimethyldichlorosilane.

The carboxyl group may be regenerated from an ester by any of the usual methods, for example, acid- and basecatalysed hydrolysis is generally applicable, as well as enzymically-catalysed hydrolyses; however, aqueous mixtures may be poor solvents for these compounds and they may cause isomerizations, rearrangements, sidereactions, and general destruction, so that special methods may be desirable.

Five suitable methods of deesterification are
1. Reactions with Lewis acids.

Suitable Lewis acids for reaction with the esters include trifluoroacetic acid, formic acid, hydrochloric acid in acetic acid, zinc bromide in benzene and aqueous solutions or suspensions of mercuric compounds. The reaction with the Lewis acid may be facilitated by addition of a nucleophile such as anisole.

2. Reduction.

Suitable systems for effecting reduction are zinc/acetic acid, zinc/formic acid, zinc/lower alcohol, zinc-/pyridine, palladised-charcoal and hydrogen, and sodium and liquid ammonia.

3. Attack by nucleophiles.

Suitable nucleophiles are those containing a nucleophilic oxygen or sulphur atom for example alcohols, mercaptans and water.

4. Oxidative methods, for example, those which involve the use of hydrogen peroxide and acetic acid.

5. Irradiation.

Where at the end of a given preparative sequence compounds are obtained wherein B is >S → O and a compound is desired in which B is > S conversion to a sulphide may for example, be effected by reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethyacetamide. The reaction may be effected at a temperature of −20° to +50° C.

Alternatively, reduction of the 1-sulphinyl group may be effected by phosphorus trichloride or tribromide in solvents such as methylene chloride, dimethylformamide or tetrahydrofuran, preferably at a temperature of −20° C to +50° C.

The acid (III) to which the acylating agent corresponds may be obtained by reacting the glyoxylic acid.

R.CO.COOH (where R has the above defined meaning) or an ester thereof with $R^aO.NH_2$ ($R^a$ having the above defined meaning).

The resulting acid or ester may then be separated into its syn and anti isomers e.g. by crystallisation, chromatography or distillation, followed when necessary by hydrolysis of the ester.

Alternatively the acid(III) where $R^a$=H may be obtained by reacting an ester of the acid

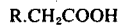

R.CH₂COOH (where R has the above defined meaning) with an inorganic or organic nitrosating agent e.g. an alkyl nitrile such as isopropyl nitrile, or nitrosyl chloride in the presence of an acid or base. We prefer that an excess of the nitrosating agent be used e.g. a molar excess. Thereafter the ester group is removed, if necessary.

Syn and anti isomers may be distinguished by appropriate techniques, e.g. by their ultraviolet spectra, by thin layer or paper chromatography or by their nuclear magnetic resonance spectra. For example, for DMSO-$d_6$ solution compounds of Formula I exhibit the doublet for the amide NH at a lower field for the syn isomers than for the anti-isomers). These factors may be employed in monitoring reactions.

The antibacterial compounds according to the invention may be formulated for administration in any convenient way, by analogy with other antibiotics and the invention therefore includes within its scope a pharmaceutical composition comprising an antibacterial compound of formula I or a non-toxic derivative e.g. salt thereof (as herein defined) adapted for use in human or veterinary medicine. Such compositions may be presented for use in conventional manner with the aid of any necessary pharmaceutical carriers or excipient.

The antibacterial compounds according to the invention may be formulated for injection and may be presented in unit dose form in ampoules, or in multidose containers with an added preservative. The compositions may take such forms as suspensions, solutions, emulsions in oily or aqueous vehicles and may contain formulatory agents such as suspending, stabilising and-/or dispersing agents. Alternatively the active ingredient may be in powder form for reconstitution with a suitable vehicle, e.g. sterile, pyrogen-free water, before use.

The compositions may be presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinyl-pyrollidone; fillers, for example lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparation may be in the form of aqueous or oily suspensions, solutions, emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats, emulsifying agents, for example, lecithin, sorbitan monooleate or acacia; non-aqueous vehicles which may include edible oils, for example, almond oil, fractionated coconut oil, oily esters, propylene glycol, or ethyl alcohol, preservatives, for example, methyl or propyl p-hydroxybenzoates or sorbic acid. Suppositories will contain conventional suppository bases, e.g. cocoa butter or other glyceride.

The composition may also be prepared in suitable forms for absorption through the mucous membranes of the nose and throat or bronchial tissues and may conveniently take the form of powder or liquid sprays or inhalants, lozenges, throat paints etc. For medication of the eyes or ears, the preparations may be presented as individual capsules, in liquid or semi-liquid form, or may be used as drops etc. Topical applications may be formulated in hydrophobic or hydrophilic bases as ointments, creams, lotions, paints, powders etc.

For veterinary medicine the composition, may, for example, be formulated as an intramammary preparation in either long acting or quick-release bases.

The compositions may contain from 0.1% upwards, preferably from 10–60% of the active material, depending on the method of administration. Where the compositions comprise dosage units, each unit will preferably contain 50–500 mg. of the active ingredient.

The dosage as employed for adult human treatment will preferably range from 100–3000 mg. for instance 1500 mg per day, depending on the route and frequency of administration.

The compounds according to the invention may be administered in combination with other therapeutic agents such as antibiotics, for example other cephalosporins, the penicillins or tetracyclines.

The following examples illustrate the invention.

2-Hydroxyimino-Acetic acids and Derivatives

Preparation 1

2-Hydroxyimino(thien-2-yl)acetic acid (syn-isomer)

A cooled solution of hydroxylamino hydrochloride (0.884 g) and sodium bicarbonate (1.08 g) in water (20 ml.) was added to a cooled (0°) solution of thien-2-yl-glyoxylic acid (2.0 g) and sodium bicarbonate (1.08 g) in water (20 ml.). After two days at 20° the solution was extracted with ether, cooled and acidified with concentrated hydrochloric acid. The resulting white solid was filtered off (0.564 g) and the filtrate was then thoroughly extracted with ether. The combined extracts were washed with brine, dried and concentrated. The solid residue was triturated with benzene to give the oxime (syn-isomer) (1.05 g; 51%), m.p. 1320,$\lambda_{max}$. (ethanol) 284 mm ($\epsilon$9,500), $\nu_{max}$. (Nujol) 2590 and 1706 ($CO_2H$) and 1655 cm$^{-1}$ (C=N), (DMSO-d6), −2.5 to −9.5 (broad multiplet; N-OH and COOH), 2.36 (multiplet; thienyl C-5 H) and 2.82 (multiplet; thienyl C-3 H and C-4 H).

Preparation 2

2-Dochloroacetoxyiminophenylacetic acid (syn-isomer).

To a mixture of methylene chloride (45 ml) and dichloroacetyl chloride (10 ml) was added portionwise with stirring 2-hydroxyiminophenylacetic acid (synisomer) (5g) in portions over about fifteen minutes. The reaction mixture became solid, and was stirred for one hour at room temperature after the addition was complete. The reaction was diluted with petroleum (b.p. 40°–60°), filtered, and the solid washed several times with petroleum spirit to remove residual acid chloride. The solid was dried under vacuum, giving 2-dichloroacetoxyiminophenylacetic acid (syn-isomer)(8.0g; 96%), m.p. 115°, $\nu_{max}$. (CHBr$_3$) 3470 and 1750 (—CO$_2$H), 1765 cm.$^{-1}$ (ester), $\tau$ (CDCl$_3$) values include 2.0 − 2.7 (multiplet; aromatic protons), 3.85 (singlet; —CHCl$_2$).

Preparation 3

2-Dichloroacetoxyimino-(thien-2-yl)acetic acid (synisomer)

2-Hydroxyimino-(thien-2-yl)acetic acid (synisomer) (38g.) was added portionwise to a stirred solution of dichloroacetyl chloride (70 ml.) in dry methylene chloride (350 ml.) at 20°. Stirring was continued and after ca. 20 mins. white fibrous crystals formed. The suspension was stirred for 10 mins. longer and then filtered. The solid was washed with methylene chloride and petroleum to give the title acid (38.5 g., 61%) $\lambda_{max}$. (EtOH) 262.5 ($\epsilon$ 9,520), 291 nm ($\epsilon$ 8,580).

Preparation 4

2-Hydroxyimino-2(thien-3-yl)-acetic acids

To a stirred solution of hydroxylamine hydrochloride (1.15 g) in methanol (15 mls) containing phenophthalein (2 drops) was added a solution of sodium methoxide in methanol until a pink colour was obtained. After the addition of one crystal of hydroxylamine hydrochloride to discharge the pink colour the mixture was added to a solution of thien-3-yl-glyoxylic acid (2.0 g) in methanol (10 mls) and refluxed for 1 hr. The methanol was evaporated to a small volume and the residue was partitioned between ethyl acetate and water. The aqueous layer was acidified to pH 1 with 2N-hydrochloric acid and extracted with ethyl acetate. After drying, the ethyl acetate was evaporated to yield a white solid consisting of isomeric 2-*hydroxyimino*-2-(*thien-3-yl*) *acetic acids*. $\lambda_{max}$. (ethanol) 254.5 nm ($\epsilon$ 9,700), $\nu_{max}$. (CHBr$_3$) 3540 (OH unbonded), 3200 (OH bonded) and 1750 cm.$^{-1}$ (COOH) $\tau$ (DMSOd$_6$) values include 1.78 [multiplet; thienyl protons (anti isomer)] 2.2 to 2.7 (complex multiplet; thienyl protons).

Preparation 5

2-Dichloroacetoxyimino-2-(thien-3-yl)acetyl chloride (syn isomer)

2-Hydroxyimino-2-(thien-3-yl)acetic (1.03 g) mixture was added portionwise to a stirred solution of dichloroacetyl chloride (1.8 mls) in dry methylene chloride (10 mls). After 30 mins. an excess of petrol (b.p. 40°–60°) was added to the reaction and the precipitated white solid was collected, washed with petrol (b.p. 40°–60°) and dried to yield 2-dichloroacetoxyimino-2-(thien-3-yl) acetic acid (syn isomer) (1.6 gms, 94%) which was suspended in dry methylene chloride and ice-cooled. To the suspension was added dropwise a freshly prepared solution of phosphorus pentachloride (1 equiv.) in dry methylene chloride. When all components were in solution the solvent was removed in vacuo at low temperature and the residual oil was azeotroped with benzene to give 2-dichloroacetoxyimino2-(thien-3-yl)acetyl chloride (syn) as a pale yellow oil which was used directly.

Preparation 6

2-Hydroxyimino-2-(fur-2-yl)acetic acids

To a stirred solution of hydroxylamine hydrochloride (1.94 gms) in methanol (30 mls) containing phenolphthalein (2 drops) was added a solution of sodium methoxide in methanol until a pink colour was obtained. After the addition of one crystal of hydroxylamine hydrochloride to discharge the pink colour the mixture was added to a solution of fur-2-ylglyoxylic acid (3.0 gm) in methanol (10 mls) and refluxed for 1 hr. The methanol was evaporated to a small volume and partitioned between ethyl acetate and water. The aqueous layer was acidified to pH 1 with 2N-hydrochloric acid and extracted with ethyl acetate. After drying, the solvent was evaporated to yield a yellow solid which was collected, washed with petrol (b.p. 40°–60°) and dried to yield an isomeric mixture of 2-hydroxyimino-2(fur-2-yl)acetic acids (2.7 gms., 81%) $\lambda_{max}$ (ethanol) 271.5 nm ($\epsilon$, 12,400), $\nu_{max}$. (CHBr$_3$) 3550 (OH), 1740 and 1705 cm.$^{-1}$ (CO$_2$H), $\tau$ (DMSO d$_6$) values include 2.62

[doublet; J 4 Hz, furyl(anti isomer) C 3-H], 2.14 and 3.32 (complex signals remaining furyl protons).

Preparation 7

2-Dichloroacetoxyimino-2-(fur-2-yl)acetyl chloride (syn)

2-Hydroxyimino-2-(fur-2-yl)acetic acid (1.38 g) mixture was added portionwise to an ice cold solution of dichloroacetyl chloride (2 8 mls.) in dry methylene chloride (14 mls.). After 15 mins stirring a white precipitate was formed which was collected, washed successively with cold dry methylene chloride and petrol (b.p. 40-60°) and dried to yield 2-dichloroacetoxyimino-2-(fur-2-yl)acetic acid (syn-isomer) (1.5 g, 63%).

To an ice-cold stirred suspension of 2-dichloroacetoxyimino-2-(fur-2-yl)acetic acid (1.5 g) in dry methylene chloride (70 mls) was added dropwise a freshly prepared solution of phosphorus pentachloride (1.0 equiv.) in methylene chloride. When solution was complete the solvent was evaporated at low temperature and the residual oil azeotroped with benzene to give 2-dichloroacetoxyimino-2(fur-2-yl)acetyl chloride (syn-isomer) as a pale yellow oil which was used directly.

EXAMPLE 1

6β-(2-Hydroxyimino-2-phenylacetamido)-2,2-dimethylpenam-3-carboxylic acid (syn-isomer)

To a suspension of 6β-amino-2,2-dimethylpenam-3α-carboxylic acid (1.08 g) in chloroform (25 ml) was added hexamethyldisilazane (2.49 g) and the mixture was heated under reflux for two hours, during which time solution occurred. The solvents were removed under reduced pressure, giving trimethylsilyl 2,2-dimethyl-6β-trimethylsilylaminopenam-3α-carboxylate as a solid. The solid was dissolved in methylene chloride (20 ml) and propylene oxide (1.5 ml) added. The solution was cooled to 0° and treated dropwise with 2-dichloroacetoxyimino-2-phenylacetyl chloride (from 1.38 g. 2-dichloroacetoxyimino-2-phenylacetic acid (syn-isomer)) in methylene chloride (20 ml), over a period of fifteen minutes with stirring. The solution was allowed to stir for 2 hours at room temperature. The solvents were evaporation under reduced pressure below 35°, and the residue taken up in ethyl acetate. After addition of methanol (2 ml), the solution was extracted as rapidly as possible with ice-cold sodium bicarbonate solution and the combined extracts washed with ethyl acetate and poured into a stirred mixture of ethyl acetate and 2N-hydrochloric acid. The organic phase was separated and combined with an ethyl acetate extraction of the aqueous phase, and the solution washed with water, dried and evaporated. The residue was taken up in ethyl acetate (5 ml) and added dropwise to petroleum (b.p. 40°-60°; 200 ml). The precipitated solid was filtered and dried, giving 6β-(2-hydroxyimino-2-phenylacetamido)-2,2-dimethylpenam-3α-carboxylic acid (syn-isomer) (0.84 g; 46%) [α]$_D$ + 210° (c 0.9,DMSO), λ$_{max.}$ (BtOH) 251 nm (ε 9,450), ν$_{max.}$ (Nujol) 3650 - 2300 (OH), 3280 (NH), 1758 (β-lactam), 1735 (CO$_2$H), 1650 and 1510 cm$^{-1}$ (CONH), τ (DMSO-d$_6$) 0.51 (doublet, J 7 Hz; NH), 2.2-2.7 (multiplet; aromatic protons), 4.28 (quartet, J 4 Hz and 7 Hz; C-6H), 4.40 (doublet J 4 Hz; C-5H), 5.27 (singlet; C-3 H), 8.39 and 8.48 (two singlets; methyl groups).

EXAMPLE 2

2,2-Dimethyl-6β-[2-hydroxyimino(thien-2-yl)acetamido]penam-3α-carboxylic acid (syn-isomer)

A solution of trimethylsilyl 2,2-dimethyl-6β-trimethylsilylaminopenam-3α-carboxylate [prepared from the corresponding amino-acid (0.864 g.)] and propylene oxide (1 ml.) in dichloromethane (20 ml.) was cooled to 0° and treated dropwise with a solution of 2-dichloroacetoxyimino(thien-2-yl)acetyl chloride syn-isomer; [prepared from the corresponding acid (0.753 g.)] in dichloromethane (12 ml.). The resulting solution was maintained at 0° for 1 hour and was then evaporated to a small bulk and partitioned between ethylacetate and saturated sodium bicarbonate solution. The aqueous phase was washed with ethyl acetate, acidified with 2N-hydrochloric acid; and extracted with ethyl acetate. The dried organic solution was evaporated to a small bulk and added dropwise to stirred petroleum spirit (b.p. 40°-60°). The resulting precipitate was collected, washed, and dried to afford the title acid (0.337 g., 24% based on amine), [α]$_D$ + 224° (c 0.57, DMSO), λ$_{max.}$ (pH 6 buffer) 288 nm (ε 6,400), λ inf. 270 nm (ε 5,800), ν$_{max.}$ (Nujol), 2600 and 1730 (CO$_2$H), 1776 (β-lactam), 1670 and 1526 cm.$^{-1}$ (CONH), τ (d$_6$-DMSO) values include 0.44 (d, J 6 Hz; NH), 2.45 and 2.9 (multiplets, aromatic protons), 5.78 (s; C-3H), 8.46 and 8.55 (2 s; CH$_3$ groups).

EXAMPLE 3

2,2-Dimethyl-6β[2-hydroxyimino-2-(thien-3-yl)acetamide] penam-3α-carboxylic acid (syn-isomer)

To a cold solution of trimethylsilyl 2,2-dimethyl-6β-trimethylsilylamino-penam-3α-carboxylate [made from 6β-amino-2,2-dimethyl-penam-3α-carboxylic acid (0.43 g) and hexamethyldisilazane (2.1 mls.)] and propylene oxide (0.53 mls) in dry methylene chloride (10 mls) was added dropwise with stirring a solution of 2-dichloroacetoxyimino-2-thien-3-yl) acetyl chloride (synisomer) (2.1 mmoles) in dry methylene chloride. After 1 hr. at 20° C the reaction was evaporated and the residue dissolved in ethyl acetate. The ethyl acetate solution was extracted with ice-cold saturated sodium bicarbonate solution. The combined aqueous phases were acidified to pH 1 with 2N-hydrochloric acid and extracted with ethyl acetate. After drying the extracts were evaporated in a small volume which on adding to an excess of petrol (b.p. 40°-60°) gave a white solid which was filtered and dried to yield the title compound (0.32 g, 44%), [α]$_D$ = +220° (c 0.9, dioxan), λ$_{max.}$ (pH 6 buffer) 256 nm (ε 9,100), ν$_{max.}$ (Nujol) 3300 (NH), 1770 (β-lactam), 1740 and 2600 (COOH) and 1660 and 1526 cm.$^{-1}$ (CONH) τ (DMSO d$_6$) includes 0.46 (d; J 8 Hz; NH) 2.30, 2.35, 2.59 (m; thienyl protons), 5.66 (s; C-3H), and 8.35 and 8.44 (2s; CH$_3$ groups).

EXAMPLE 4

2,2-Dimethyl-6β-[2-hydroxyimino(fur-2-yl)acetamido]-penam-3α-carboxylic acid (syn-isomer)

A solution of trimethylsilyl 2,2-dimethyl-6β-trimethylsilylaminopenam-3α-carboxylate [prepared from the corresponding amino-acid (0.648 g.)] and propylene oxide (0.75 ml.) in dichloromethane (15 ml) was cooled to 0° and treated dropwise with a solution of 2-dichloroacetoxyimino(fur-2-yl)acetyl chloride

[synisomer; prepared from the corresponding acid (0.579 g.)] in dichloromethane (12 ml.). The resulting solution was maintained at 0° for 1 hour and was then evaporated to small volume and partitioned between ethylacetate and saturated sodium bicarbonate solution. The aqueous phase was washed with ethyl acetate, acidified with 2N-hydrochloric acid and extracted with ethyl acetate. The dried organic solution was evaporated to a small bulk and added dropwise to stirred petroleum spirit (b.p. 40°–60°). The resulting precipitate was collected, washed and dried to give the title acid (0.56 g., 55% based on amine), $[\alpha]_D$ + 243° (c 0.93, DMSO), $\lambda_{max.}$ (pH 6 buffer) 275 nm ($\epsilon$ 9,600), $\nu_{max.}$ (Nujol), 1778 ($\beta$-lactam), 1740 and 2600 ($CO_2H$), 1670 and 1528 cm.$^{-1}$ (CONH), $\tau$ ($d_6$-DMSO) values include 0.44 (d, J 6 Hz; NH) 2.18 and 3.34 (multiplets; aromatic protons), 5.70 (s; C-3H), 8.36 and 8.46 (2s; $CH_3$ groups).

We claim:

1. A compound selected from the group consisting of a penicillin antibiotic of the formula

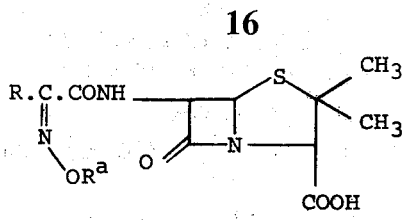

wherein R is phenyl or phenyl substituted by chloro, bromo, hydroxy, lower alkyl, nitro, amino, lower alkylamino, di(lower alkyl)amino, lower alkanoyl, lower alkanoylamido, lower alkoxy, lower alkylthio or carbamoyl; and $R^a$ is hydrogen or

wherein $R^c$ is $C_1$–$C_4$ alkyl, $C_1$–$C_4$ chloroalkyl, $C_1$–$C_4$ alkoxy, phenyl, nitrophenyl, $C_1$–$C_4$ alkylamino or $C_1$–$C_4$ chloroalkylamino; and a physiologically acceptable salt thereof, said penicillin antibiotic being in the form of the syn isomer free of the corresponding anti isomer to the extent of at least 75%.

2. The compound of claim 1 which is 6$\beta$-(2-hydroxyimino-2-phenylacetamido)-2,2-dimethylpenam-3$\alpha$-carboxylic acid (syn isomer).

* * * * *